United States Patent [19]
Godik

[11] Patent Number: 5,865,167
[45] Date of Patent: Feb. 2, 1999

[54] METHOD OF LIVING SYSTEM ORGANISM DIAGNOSTICS AND APPARATUS FOR ITS REALIZATION

[75] Inventor: Eduard E. Godik, Washington Township, N.J.

[73] Assignee: Dynamics Imaging, Inc., Devon, Pa.

[21] Appl. No.: 565,747

[22] Filed: Nov. 30, 1995

Related U.S. Application Data

[63] Continuation of Ser. No. 116,472, Sep. 3, 1993, abandoned.

[51] Int. Cl.$^6$ ........................................................ A61B 5/00
[52] U.S. Cl. ............................ 128/133; 600/473; 600/476
[58] Field of Search ............................ 128/633, 664–667; 356/39–41; 600/310, 473, 474, 475, 476–479

[56] References Cited

U.S. PATENT DOCUMENTS

| | | | |
|---|---|---|---|
| 3,878,392 | 4/1975 | Yew et al. | 250/306 |
| 3,897,150 | 7/1975 | Bridges et al. | 356/5 |
| 4,207,901 | 6/1980 | Nigam | 128/660 |
| 4,212,306 | 7/1980 | Mahumud | 128/665 |
| 4,281,645 | 8/1981 | Jöbsis | 128/633 |
| 4,286,602 | 9/1981 | Guy | 128/665 |
| 4,312,357 | 1/1982 | Andersson et al. | 128/664 |
| 4,385,634 | 5/1983 | Bowen | 128/653 |
| 4,434,799 | 3/1984 | Taenzer | 128/660 |
| 4,495,949 | 1/1985 | Stoller | 128/664 |
| 4,515,165 | 5/1985 | Carroll | 128/664 |
| 4,536,790 | 8/1985 | Kruger et al. | 358/111 |
| 4,570,638 | 2/1986 | Stoddart et al. | 128/665 |
| 4,573,472 | 3/1986 | Ito | 128/399 |
| 4,576,173 | 3/1986 | Parker et al. | 128/633 |
| 4,583,869 | 4/1986 | Chive et al. | 374/122 |
| 4,649,275 | 3/1987 | Nelson et al. | 250/358.1 |

(List continued on next page.)

FOREIGN PATENT DOCUMENTS

| | | |
|---|---|---|
| 0447708A3 | 9/1991 | Japan . |
| WO79/00594 | 8/1979 | WIPO . |

OTHER PUBLICATIONS

Godik, E.E., Guljaev, Yu.V., "The Human Being Through 'Eyes of Radiophysics'", *Journal of Radio Engineering* (Russian) 1991, No. 8, pp. 51–62.

Ring, E.F.J. and Hughes, H. "Real Time Video Thermography", in *Recent Developments in Medical and Physiological Imaging* a supplement to Journal of Medical Engineering and Technology, 1986, pp. 86–89.

Platonov, S.A., . . . , Godik, E.E., "Informative Tasks of Functional Mapping of Biological Subjects", *Journal of Radio Engineering* (Russian) 1991, No. 8, pp. 62–68.

Jacquez, J.A. et al, "Spectral Reflectance of Human Skin in the Region 235—1000 nm", *Journal of Applied Physiology*, 1955, vol. 7, No. 3, pp. 523–528.—copy not available.

"Physics of Image Visualization in Medicine", C. Webb, ed. vol. 2, pp. 241–243.—copy not available.

(List continued on next page.)

*Primary Examiner*—Jennifer Bahr
*Assistant Examiner*—Bryan K. Yarnell
*Attorney, Agent, or Firm*—Jacob E. Erlich; Jerry Cohen

[57] ABSTRACT

A method of diagnostics of living organism state and an apparatus for its realization, comprising the steps of (i) illuminating living organism surface (1) with electromagnetic radiation from source (2) of optical wavelength range from 0.3 to 2.0$\mu$, (ii) receiving transmitted through or back scattered by the living organism radiation by detectors (3 and 4), (iii) with the help of sequentially connected commutator (5), analog-to-digital converter (6) and input-output controller (7), spatial distribution of at least one parameter, characterizing transmittance and/or back scattering by living organism radiation in the computer system (8) is performed sequentially and continuously in time. At the above mentioned spatial distributions, spatial regions are revealed, differing from each other by at least one parameter, characterizing their temporal changes, and the revealed regions are recorded as a functional map of physiological processes taking place in living organism.

46 Claims, 8 Drawing Sheets

U.S. PATENT DOCUMENTS

| | | | |
|---|---|---|---|
| 4,767,928 | 8/1988 | Nelson et al. | 250/341 |
| 4,774,961 | 10/1988 | Carr | 128/736 |
| 4,798,209 | 1/1989 | Klingenbeck et al. | 128/653 |
| 4,807,637 | 2/1989 | Bjorkholm | 128/664 |
| 4,810,875 | 3/1989 | Wyatt | 250/227 |
| 4,817,038 | 3/1989 | Knoll et al. | 364/413.24 |
| 4,817,622 | 4/1989 | Pennypacker et al. | 128/664 |
| 4,829,184 | 5/1989 | Nelson et al. | 250/358.1 |
| 4,862,894 | 9/1989 | Fujii | 128/666 |
| 4,927,244 | 5/1990 | Bahr et al. | 350/350 S |
| 4,945,239 | 7/1990 | Wist et al. | 250/358.1 |
| 4,948,974 | 8/1990 | Nelson et al. | 250/358.1 |
| 4,955,383 | 9/1990 | Faupel | 128/653 R |
| 4,995,398 | 2/1991 | Turnidge | 128/668 |
| 5,079,698 | 1/1992 | Grenier et al. | 364/413.13 |
| 5,099,848 | 3/1992 | Parker et al. | 128/661.07 |
| 5,139,025 | 8/1992 | Lewis et al. | 128/665 |
| 5,170,119 | 12/1992 | Sekihara et al. | 324/260 |
| 5,197,470 | 3/1993 | Helfer et al. | 128/634 |
| 5,213,105 | 5/1993 | Gratton et al. | 128/664 |
| 5,222,495 | 6/1993 | Clarke et al. | 128/633 |
| 5,269,325 | 12/1993 | Robinson et al. | 128/653.1 |
| 5,293,873 | 3/1994 | Fang | 128/664 |
| 5,301,681 | 4/1994 | DeBan et al. | 128/736 |
| 5,303,026 | 4/1994 | Strobl et al. | 356/318 |
| 5,305,748 | 4/1994 | Wilk | 128/653.1 |
| 5,307,807 | 5/1994 | Valdes Sosa et al. | 128/653.1 |
| 5,309,907 | 5/1994 | Fang et al. | 128/633 |
| 5,311,018 | 5/1994 | Zana et al. | 250/330 |
| 5,313,941 | 5/1994 | Braig et al. | 128/633 |
| 5,333,610 | 8/1994 | Hirao | 128/633 |
| 5,337,745 | 8/1994 | Benaron | 128/633 |
| 5,371,368 | 12/1994 | Alfano et al. | 250/341.1 |
| 5,515,847 | 5/1996 | Braig et al. | 128/633 |
| 5,572,996 | 11/1996 | Doiron et al. | 128/633 |

OTHER PUBLICATIONS

Krenkel, T.E., Kogan, A.G. and Tatatorian, A.M., "Personal Computers in Engineering", Izd. Mir, RiS, (Russian) 1989, p. 71.—copy not available.

Dgagupov, R.G. and Erofeev, A.A., *Piezo–Ceramic Elements in Instrument Designing and Automatics*, Leningrad, Izd. Mashinosroenie, 1986, pp. 154–155 (Russian).—copy not available.

Svechnikov S.V. "Optoelectronics elements", Moscow, Izd. Sov. Radio 1971, pp. 250–256.—copy not available.

Legett, Kate, *Optical mamography offers promise as alternative to x–ray detection*, Biophotonics International, Jan./Feb., 1996, pp. 56–57. This publication has been submitted as representative of a recent development in the field of mamography.

Godik, Eduard E. and Gulyaev, Uri, V., "Functional Imaging of the Human Body," *IEEE Engineering in Medicine and Biology*, Dec. 1991, pp. 21–29.

*Physics of image visualization in medicine*, C. Webb, ed., vol. 2, p. 382, Moscow, Mir, 1991 (Translated from English) (copy not available).

*The comparison of the sensitivity of ultrasound echo and shadow methods for determination of calcification of breast tissues*, Proc. Conf. Ultrasound Biology & Medicine—Ubiomed. VI, Warsaw–Jablonna, Sep. 19–23, 1983, pp. 41–49 (copynot available).

Ichimury, A. *Wave propagation and scattering in randomly inhomogeneous media*, vol. 1, pp. 74–79, Moscow, Mir, 1981 (Translated from English) (copy not available).

Barabanenkov, Yu. N. *On the relative increase in radiation extinction length due to correlation of weak scatterers*, USSR Academy of Sci. Proceedings, Physics of atmosphere and ocean, vol. 18, No. 7, pp. 720–726, 1982 (copy not available).

Vartapetjan, M.A. et al. *Sensor perception. An investigation experience with the help of focused ultrasound*, Leningrad, Nauka, 1985 (Russian).

*Biophysical approach to the problem of safety under the ultrasound diagnostics*, Proc. Conf. Ultrasound Biology & Medicine—Ubiomed. YI, Warsaw–Jablonna, Sep. 19–23, pp. 95–99, 183 (copy not available).

Titce, U. and Shenck, K. *Semiconductor scheme technology*, p. 144, Moscow, Mir, 1982 (Translated from English to Russian) (copy not available).

Krenkel, T.E. et al. *Personal computers in engineering practices*, pp. 71–75, Moscow, RiS, 1989 (Russian) (copy not available).

Guljaev, Yu.V., Godik, E.E. et al. *On the possibilities of the functional diagnostics of the biological subjects via their temporal dynamics of the infrared images*, USSR Academy Nauk Proceedings/Biophysics—1984, vol. 277, pp. 1486–1491 (copy not available).

Hasset, J. *Introduction into psycho–physiology*,—Moscow, Mir, 1981 (Translated into Russian) (copy not available).

Godik, E.E., Guljaev, Yu.V. *Human and animal physical fields*, V mire nauki (Russian version of Scientific American)/1990, No. 5, pp. 74–83 (copy not available).

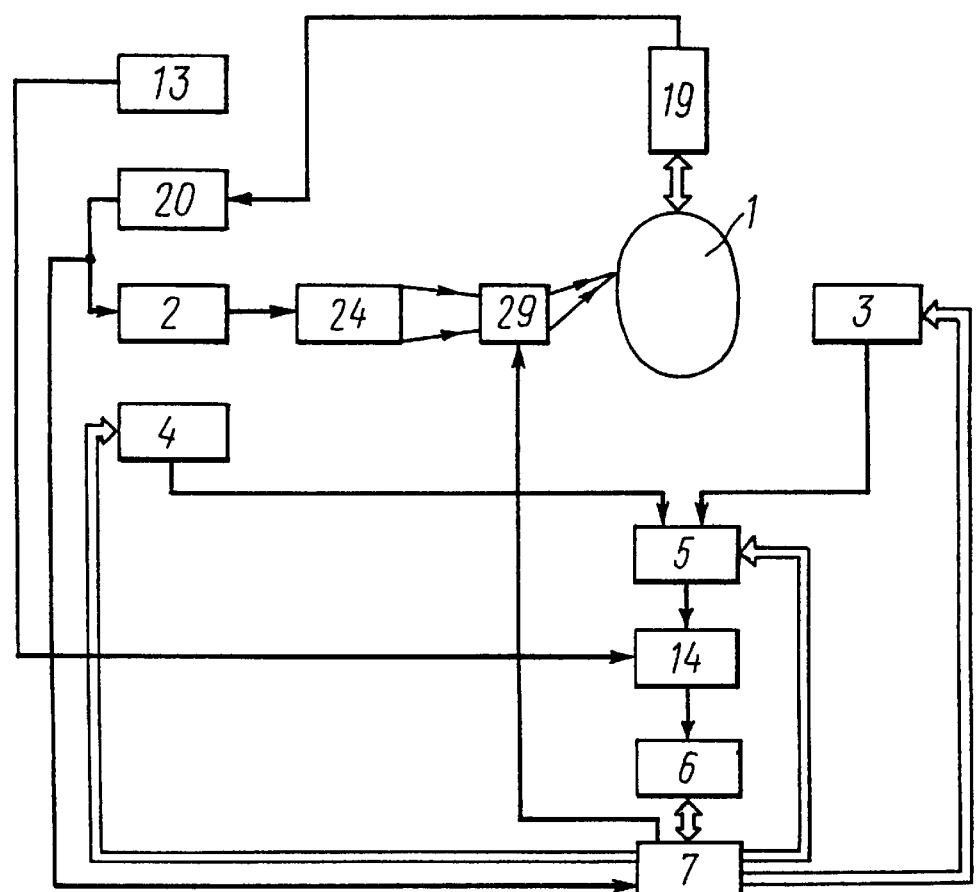
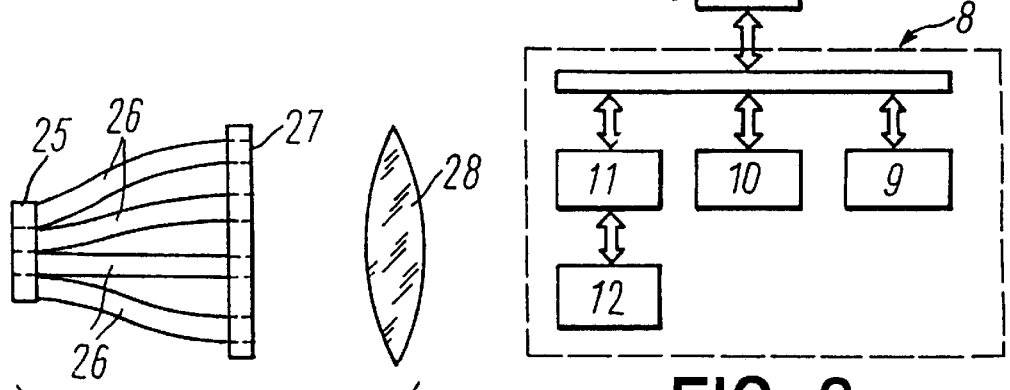
FIG. 7
FIG. 8

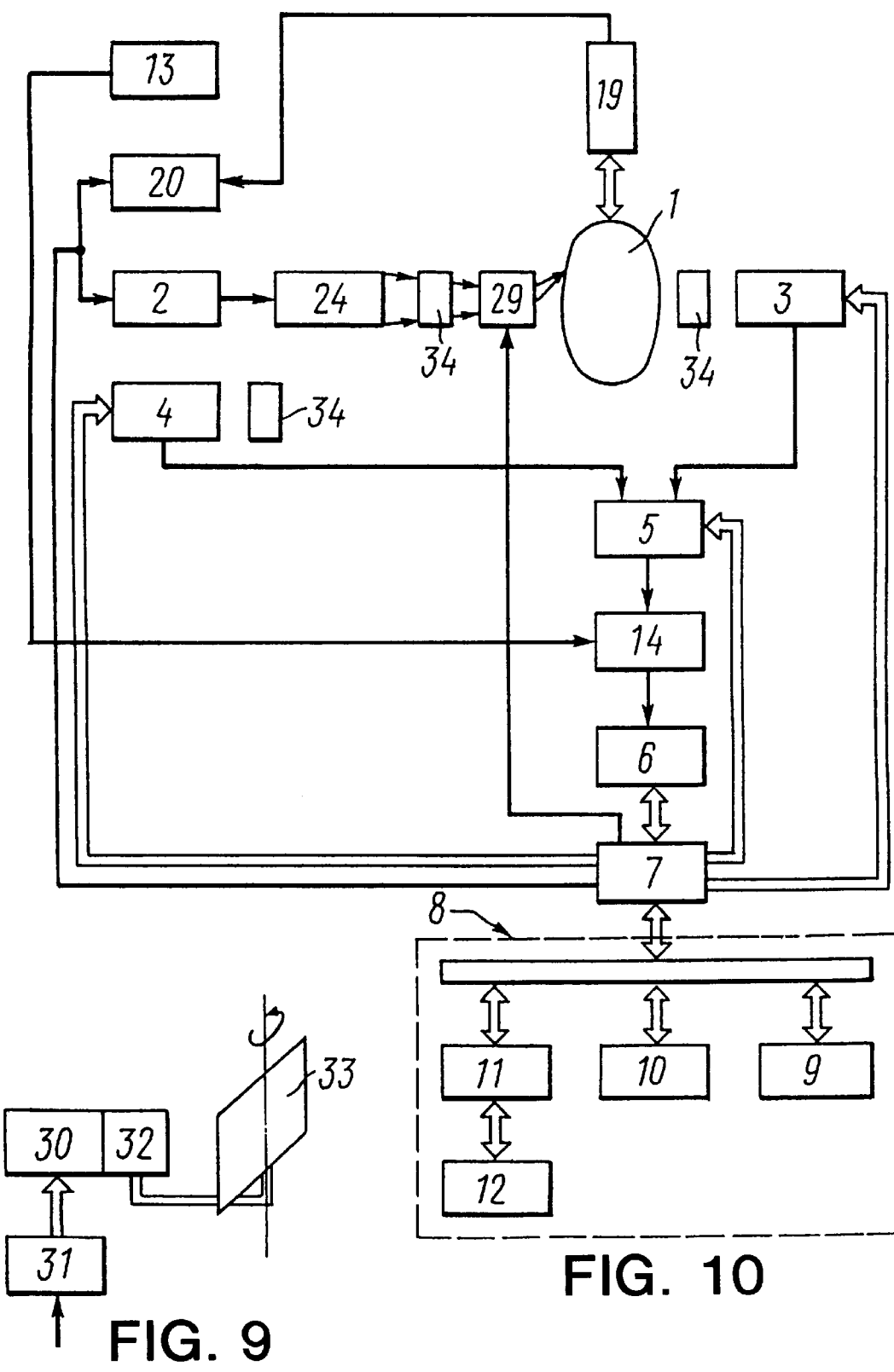

METHOD OF LIVING SYSTEM ORGANISM DIAGNOSTICS AND APPARATUS FOR ITS REALIZATION

CROSS REFERENCE TO RELATED APPLICATIONS

This application is a continuation of U.S. patent application Ser. No. 08/116,472 filed Sep. 3, 1993 and now abandoned.

BACKGROUND OF THE INVENTION

The present invention belongs to the field of physics and medicine, or more precisely, to methods and apparatus for obtaining information about physiological processes taking place in living organisms. It relates to a method of living organism state diagnosis and apparatus for its realization which could be used for the investigation and diagnosis of the functional dynamics of a living organism's physiological processes.

Functional dynamics is defined as a measure of the homestatic stability of a living organism. Functional diagnosis means using a measure or measures of functional dynamics to diagnose possible pathological conditions in a living organism. Using functional diagnosis as a diagnostic procedure has the potential to detect early precursors of pathology by revealing subtle disturbances in the relationships between physiological systems. Early detection of a pathological condition makes likelier the avoidance of non-reversible disturbances in a living organism and therefore avoids radical treatment methods. For this reason, methods of early functional diagnostics are acquiring increasing significance for population screening and development of preventive medicine.

The state of living organism is reflected in the continuous functional dynamics of its biological tissues. These dynamics are determined by the functioning of the main distributed physiological systems, such as cell metabolism, which supplies the tissues with energy, and microcirculation, which supplies their metabolic resources. The functional status of these main life supporting tissue systems is determined by distributed regulatory mechanisms, which function both for the whole organism and at the cellular level. Cell metabolism is connected with microcirculation via one important distributed tissue system-perfusion. Since the perfusion system interconnects the first two systems, study of the functional dynamics of the perfusion system will reveal important information on the state of the living organism both for the whole organism and at the cellular level.

The state of the whole-organism systems is reflected not only and not exclusively by tissue functional dynamics at separate organism sites, but mainly by the degree and the character of the spatial synergy of these dynamics. To explore this synergy of tissue physiological processes characterizing the whole-organism functional status, the investigation of continuous spatial distribution of functional dynamics of microcirculation is necessary. In the relaxation state, for example, spatial synergy of the functional dynamics in the process of tissue activity is minimal, whereas it is greatly increased under the stress conditions.

Each physiological parameter has its own physical image, or physical "projection".

Integral cell metabolism and microcirculation intensity in each organism site is reflected by its temperature value. In addition, one of the most informative physical parameters, reflecting the state of biological tissues of a living organism, is their complex dielectric permeability. Its imaginary part, the absorption coefficient of electromagnetic (EM) radiation by biological media, is characterized by a specific spectral dependence in the optical range on the main physiological agent of microcirculation—hemoglobin and its different functional forms: oxy-hemoglobin and carboxy-hemoglobin, as well as for cytochrome aa3, which also participates in cell metabolism. In a very wide range of EM-radiation frequencies, the real part of dielectric permeability depends on the degree of blood content in tissues and characterizes tissue functional inhomogeneity, produced, for example, by microcirculation dynamics.

In order to measure the temperature and dielectric characteristics of biological tissues, different physical methods are applied for functional diagnostics investigations. For non-invasive measurements of biological tissues' temperature, their electromagnetic thermal radiation is registered. The latter is the most intensive in the middle infrared (IR) range, which makes it possible to measure tissues temperature with the necessary accuracy of 0.1 degree. This is the essence of infrared dynamic thermovision, which permits investigation of spatial distribution of living organism tissue functional dynamics.

In this method, (Godik E., Gulyaev, "Functional Imaging of the Human Body," IEEE Engineering in Medicine and Biology," 1991) temporary changes in spatial distribution of IR-thermal radiation intensity of living organism tissues are registered, reflecting their spatial-temporal microcirculation dynamics in the form of a temporal sequence of thermoimages. This is performed both in the process of natural organism functioning and in the process of physiological reactions on different functional probes: reflective and humoral ones. For example, pain reactions or the influence of pharmaceutical treatments can be visualized via such procedures; the regions with different regulation disturbances can be revealed, differentially diagnosing which type of regulation is disturbed: reflective or humoral one. Also, the state of internal organs can be estimated by specific reactions of the corresponding dermatomes (Zakharjin-Ged skin zones). However, IR-thermovision method has a number of significant restrictions, as outlined below.

First, IR-thermal radiation carries direct information on physiological processes only in skin, since its characteristic absorption depth does not exceed $100\mu$. The method taught by Jobsis in U.S. Pat. No. 4,281,645 "Method and Apparatus for Monitoring Metabolism in Body Organs," attempts to overcome this limitation by transilluminating the body and integrating over a long path length. However, functional changes in blood content in skin capillary nets, disposed at the depth of $0.5\mu$ or larger, are reflected in skin temperature by means of thermoprojection, due to which a delay and inertia of several seconds emerges. That is why IR-thermal radiation does not reflect practically blood flow functional dynamics, connected, for example, with cardio- and respiratory pulsation, since thermoprojection time is several seconds. Second, the temperature reflects blood flow and metabolism contributions simultaneously and integrally, which does not permit differential diagnostics of their disturbances. Third, the middle IR-range technology, necessary for the realization of the above method, is unreasonably expensive.

For dielectric permeability measurements, the investigated part of the living organism is illuminated with EM-radiation and parameters of back scattered and/ or transmitted radiation are measured. EM-radiation of optical wavelength range—from 0.3 to $1.3\mu$ wavelengths is effectively used for biological tissue investigation. At near IR wavelength range from 0.65 to 1.0µ the tissues are transparent enough to be seen at depth of more than one centimeter. This transparency is limited by light scattering, with the characteristic weakening of such radiation making the 3–5µ range unusable for water-containing tissues. The absorption depths for the above mentioned physiological pigments reach up to several centimeters; in spite of the low absorption in the above region, it is selective enough to separate the contributions from the different pigments. For the wavelengths longer than 1.2µ the transparency of water-containing tissues decreases sharply as a result o f the strong water absorption.

The photopletismography method is well known (U.S. Pat. No. 4927244). The essence of this method is that the region under investigation, mostly the thinnest and thereby easier transilluminated body parts—ear lobes or hand and leg finger tips, are illuminated by EM-radiation of the above mentioned wavelength range; the intensity of transmitted and/or back scattered radiation is measured; the ratio of the latter intensities and that of the illuminating radiation (transmittance and back scattering coefficients, respectively) are calculated as a continuous functions of time; temporal dependencies of these coefficients, originating from cardiopulsation, arc analyzed; functional state of microcirculation is judged from the extremum positions and the amplitudes ratio. This method is similar to that taught by Parker, et al. in U.S. Pat. No. 4,576,173 "Electro-Optical Device and Method for Monitoring Instantaneous Singlet Oxygen Concentration Produced During Photoradiation Using a CW Excitation Source."

These methods, however, are based on the analysis of the microcirculation functional mechanics at separate organism sites and do not permit estimation of microcirculation over the organism surface, or the spatial picture of its interconnection within the organism scope. Thus there exists no potential to estimate the state of the organism's health based on the interaction of separate physiological systems.

More weighty information on the functional microcirculation dynamics and cell metabolism in separate organism sites could be obtained using the method of spectral monitoring of biological tissues in the near IR-wavelength range (U.S. Pat. No. 5,303,026, Strobl, et al, "Apparatus and Method for Spectroscopic Analysis of Scattering Media"). To realize this method, the part of living organism under investigation is alternatively illuminated by radiation of several wavelengths in the range from 0.6µ to 1.0µ; the intensity of transmitted and/or back scattered radiation is measured for each wavelength as a continuous function of time; coefficients of transmittance and/or back scattered radiation are determined for each wavelength; the system of differential equations is solved with the use of these data and temporal dependencies of oxyhemoglobin, carboxyhemoglobin and cytochrome aa3 are calculated. The character of these dependencies is analyzed in the process of physiological reactions on different functional tests both local ( i.e. applying a blood pressure cuff) and the whole-organism ones. The obtained dependencies are compared with similar ones for a healthy person and the presence of pathology is judged by the deviations in the reaction amplitudes and the time delays. This method permits more detailed analysis of the functional state of the living organism to be performed to reveal not only disturbances in the functional microcirculation mechanics, but also deviations in oxygenation status of the tissue investigated, in the ratio of arterial and venous blood content, in the perfusion state—by a delay in time dynamics and by the amplitude ratio of changes in oxyhemoglobin and cytochrome aa3 concentrations. This extends significantly the potential to revel pathology and its differential diagnostics.

However, this above described method as well as the previous one permits estimation of the character of functional dynamics of physiological processes only at separate organism points and does not make it possible to visualize and to investigate a continuous spatial synergy of these processes in a whole organ or in the organism as whole.

A method and apparatus are known which permit the determination of the optical properties of living organism tissues (U.S. Pat. No. 4,515,165). To realize this method, the part of living organism under investigation, a mammary gland, for example, is illuminated by electromagnetic radiation of optical wavelength range (near IR-range), transmitted radiation is acquired and the spatial distribution of its intensity is registered. This method reveals pathological inhomogeneities in transparency of living organism tissues but only of sufficiently large size and located not too deep from the surface, and happen to be turned to the radiation detector. Tumors of the mammary gland, for example, are able to be discovered with method, as a rule, too late, when they have already reached a large size .

The method proposed by Bowen in U.S. Pat. No. 4,385,634 "Radiation-Induced Thermoacoustic Imaging" describes the possibility of increasing the spatial resolution to reveal pathological changes in tissue morphology (structure) but not in physiological dynamics.

Thus, currently used methods permit investigation of spatial synergy of the functional dynamics of physiological processes only in skin, either only morphological changes in a tissues depth in one (or a few) frame or functional changes in separate preselected points. All methods reviewed yield insufficient information for differential diagnostics based on partial contributions of microcirculation and metabolic thermoproduction. Methods that permit a detailed investigation of pre-capillary blood flow and cell metabolism only provide it at separate discrete points.

SUMMARY OF THE INVENTION

The present invention is directed to creation of a new method and apparatus for investigation of functional dynamics of physiological processes in living organisms where living organisms denote parts of the organism such as organs or tissues or the entire organism. This method permits diagnosis of both the tissue functional state and homeostatic stability of the living organism as whole via the character of continuous temporal-spatial distribution of externally measured physical parameters of the living organism.

This task is solved by the method according to which a living organism or a part of it is illuminated by electromagnetic radiation of the optical wavelength range. Electromagnetic radiation of the optical wavelength range which has been transmitted though the organism and/or back scattered is received and registered in the form of an image. This image consists of the spatial distribution of at least one parameter, characterizing transmittance and/or back scattering of electromagnetic radiation of optical wavelength range by the living organism. According to the invention, the above spatial distribution is registered sequentially and continuously in time. This permits obtaining information on spatial distribution of the functional dynamics of arterial and venous capillary blood content. The spatial distribution of the transparency and/or back scattering coefficients of the electromagnetic radiation by the living organism could also be registered.

The above electromagnetic radiation can be modulated by amplitude and the transmitted and/or back scattered electromagnetic radiation is then received synchronously at the modulation frequency. This avoids the influence of background light and the necessity to perform measurements in a special darken room.

The above mentioned electromagnetic radiation can be modulated by amplitude synchronously with one of the living organism physiological rhythms to thereby realize stroboscopic registration of the back scattered or transmitted radiation. This improves the visualization contrast of the pulse wave, for example.

To obtain information from different depth from the illuminated surface, the electromagnetic radiation is concentrated at least at one point of the living organism surface and radial distribution of the characteristics of radiation back scattered by and/or transmitted through the investigated field are registered.

The surface of the illuminated living organism can be scanned with the electromagnetic radiation concentrated at least at one point. This makes it possible to improve the spatial contrast.

The electromagnetic radiation which illuminates the living organism can be filtered by frequency in the range of physiological pigments absorption. This permits separation of the partial image dynamics connected with microcirculation functioning and cell metabolism.

The frequency filtering can be performed at least for a one band from the wavelength range from 0.38 to $0.48\mu$ and/or from 0.52 to $0.62\mu$, which permits separation of the image dynamics produced by hemoglobin absorption. The filtering could also be performed from the $0.6\mu$ to $0.75\mu$ range, which permits separation of the image dynamics connected with deoxygenated hemoglobin absorption or from the range of $1.0\mu$ to $1.1\mu$, which permits separation of the image dynamics connected with oxy-hemoglobin absorption.

Transmitted and/or back scattered electromagnetic radiation can be also be filtered by frequency in the range of absorption of physiological pigments, which permits, similar to the case of the illuminating radiation filtering, separation the partial image dynamics connected with microcirculation functioning and cell metabolism.

In such a case, filtering can also be performed for at least one band from the wavelength range of $0.38\mu$ to $0.48\mu$ and/or in the range of $0.6\mu$ to $0.75\mu$, which permits separation of the image dynamics connected with hemoglobin absorption. Filtering can also be performed in the range of $0.52\mu$ to $0.62\mu$ which permits separation of the image dynamics connected with deoxygenated hemoglobin or in the range of $1.0\mu$ to $1.1\mu$, which permits separation the image dynamics connected with oxyhemoglobin absorption.

The electromagnetic radiation can be modulated by frequency and the transmitted and/or back scattered radiation received synchronously at the modulation frequency.

The electromagnetic radiation can be modulated by the frequency at least at one band from the wavelength range from $0.6\mu$ to $0.65\mu$, which permits separation of the image dynamics connected with oxyhemoglobin absorption, and also at the wavelength range from $0.65\mu$ to $0.72\mu$, which permits separation of the image dynamics connected with deoxygenated hemoglobin absorption. In the above described spatial distributions sequentially registered in time, regions can be distinguished which differ from each other at least by one of the parameters, characterizing their variation in time, and a set of the revealed regions can be registered in the form of a functional map of physiological processes of the living organism. This permits separation of the regions with a high correlation level of functional dynamics.

As a distinctive parameter, at least one parameter is calculated which characterizes the transmittance and/or back scattering of the electromagnetic radiation at different points of the investigated region of the living organism. Parameters which can be calculated are: the time cross-correlation coefficient, the velocity of the wave-like changes, the frequency of changes in time, the time delay, or the number and location of the extremum in temporal dynamics.

The registration of the functional dynamic maps can be performed synchronously with one of the natural physiological rhythms of the living organism. This permits the improvement of the separation of dynamics under the presence of radiation scattering from the surface layers of living organism. As natural physiological rhythms of the living organism, breathing rhythm, rhythm of cardiopulsation or muscle tremor could be used.

Functionally connected living organism parts are to be mapped simultaneously. This permits revealing the character of functional connectivity both between the regions, for example, between motor area of the brain cortex and skeletal muscles, or between internal organs and dermatomes reflexively connected with them. Paired organs of living organism are mapped simultaneously. This gives the possibility of revealing abnormalities in nervous and/or humoral regulation, or of detecting tumors which are characterized by a change in functional dynamics.

At least one external stimulus is applied in the process of illumination of a living organism or a part of it by the electromagnetic radiation. The application of corresponding stimuli permits contributions from the various physiological systems to be distinguished one from another. External stimuli can include, for example, changes in physical parameters of the environment, changes in external breathing parameters, the composition of gas mixture breathed in by living organism, vibration, electric field, alternating magnetic field, physical exercises, ultrasound, alternating pressure and thermal radiation can all be used.

The apparatus to accomplish the above task contains a source of optical radiation and a detector of radiation transmitted by the living organism located at a point which is opposite the source of illumination, successively connected with a analog-to-digital converter, a commutator, an input/output controller and a computer system. The apparatus also contains, according to the invention, an additional detector of back scattered radiation situated at the same side as the source of optical illumination successively connected with a analog-to-digital converter, the other input of the commutator, the input/output controller and the computer system.

The apparatus can contain a reference detector of the optical radiation, optically connected with the illumination source, and a divisor, included between the commutator output and an input of analog-to-digital converter, the output of the referent detector being connected with the other input of the divisor.

The apparatus can contain successively connected sensor (s) of at least one of the natural living organism physiological rhythms and a temporal modulator, output of which is connected with an input of optical radiation and with corresponding input of an input/output controller. The sensor of natural living organism rhythms can be a detector of breathing rhythm, rhythm of cardiopulsation and muscles tremor of the living organism.

The apparatus can contain an optical system, located between optical illumination source and the living organism surface, focusing optical radiation at least at one point of the living organism surface.

The apparatus can contain a scanning system, optically connected with the optical one, whose input is connected with the corresponding output of the input-output controller.

The apparatus can contain at least one optical filter, located at the same optical axis as that of the optical illumination source and between the latter and the surface of living organism illuminated.

The apparatus can contain at least one optical filter, located at same optical axis as that of the detector of scattered radiation and between the above detector and the surface of living organism investigated.

The apparatus can contain a frequency modulator, the output of which is connected with the source of optical radiation, and the input with the corresponding output of the input-output controller.

BRIEF DESCRIPTION OF THE DRAWINGS

Below, the invention is explained by an example of its realization and by the figures, in which:

FIG. 7 is a diagram of one of the possible variants of the optical system;

FIG. 8 is a general block diagram of a set-up for investigation of functional dynamics of living organism physiological processes with scanning, according to the invention;

FIG. 9 is one of the possible variants of the scanning system;

FIG. 10 is a general block diagram of a set-up for investigation of functional dynamics of living organism physiological processes with filtering, according to the invention;

DETAILED DESCRIPTION OF THE PREFERRED EMBODIMENTS

Figure 1:
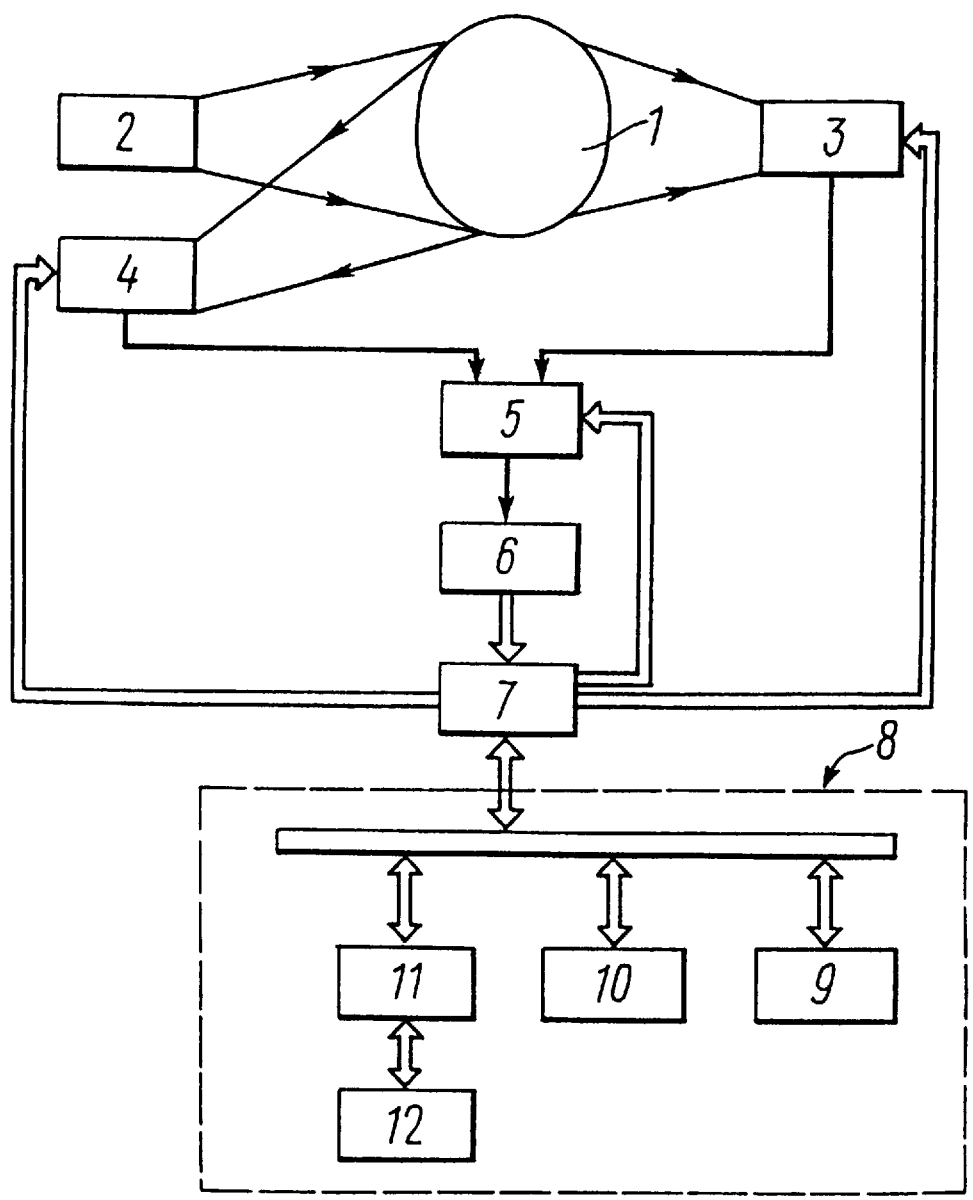
FIG. 1 is a general block diagram of a set-up for investigation of functional dynamics of living organism physiological processes, according to the invention.

In order to realize the suggested method, a living organism or a part of it is illuminated with electromagnetic radiation of the optical wavelength range from 0.3 to 2.0$\mu$. The radiation transmitted through the living organism and/or back scattered by it is then received and recorded in the form of the temporal sequences of images or maps of the spatial distributions of at least one parameter, characterizing transmittance and/or back scattering of the radiation by living organism. For example, the intensity of transmitted and back scattered radiation is dependent on arterial and venous blood content. The degree of the optical radiation absorption by a healthy tissue and pathological one, tumor for example, is different, that is why the spatial intensity distributions carry information on the presence of tumors.

Living organism tissues are diffusely scattering media as far as optical radiation in the visible range is concerned, and this considerably complicates the localization of the pathological inhomogeneities situated near the illuminated surface of living organism. Therefore, simultaneous registration of the intensity of back scattered radiation from the illuminated side and radiation transmitted through the region investigated gives additional information on the localization of pathological inhomogeneities, including tumors.

The above mentioned maps of the intensity spatial distribution are registered sequentially continuously in time, which gives information about temporal-spatial functional dynamics of arterial and venous capillary blood content. Under these conditions, the time of recording of each of such instant maps must be much less than the minimal time constant of the investigated physiological processes or time intervals between their functional dynamics extrema. For securing continuous recording of such dynamic mapping in time, the time interval between the maps must be much less than the minimal time constant of the investigated physiological process or time intervals between extrema of its functional dynamics, which should be larger, however, than the map recording time. Such a procedure is called dynamic mapping. For securing continuous registration of the each map all over the space investigated, the distance between the measurement points must be much less than the characteristic length of cross-correlation of the dynamic field investigated or the spatial scale of its variability. It should be noted that discrete intervals for space and time, necessary for securing of continuous temporal-spatial imaging of a living organism, in general are not independent of each other: if nerve control processes—with the time constants of several seconds—have some certain value of the spatial cross-correlation length, then humoral control ones - with the time constant of several minutes—have in general a quite different one. The temporal sequence of images or maps obtained as a result of dynamic mapping we call a dynamic image.

As a parameter one can use the characterizing transmittance and/or back scattering of the above mentioned radiation by a living organism, or the coefficients of transmittance and/or back scattering equal to the ratio of intensities of the transmitted and/or back scattered radiation and the illuminating radiation. In many cases, to reflect spatial-temporal dynamics of back scattering and/or transmittance of the radiation by the investigated region, it is convenient to use, instead of back scattering and transmittance coefficients, just the relative changes in the intensities of back scattered and/or transmitted electromagnetic radiation.

To exclude background light and the necessity of performing the measurements in darken rooms, the amplitude modulation of illuminating radiation and synchronous detection at the modulation frequency is applied, if necessary. The modulation frequency of the radiation intensity is chosen to be much larger than the natural physiological rhythms, including cardiopulsations. Under these conditions, a synchronous detection of the transmitted and/or back scattered radiation at the modulation frequency is used. The relative instability of the radiation amplitude modulation must be less than the relative changes in the radiation transmittance and back scattering coefficients.

The distributions of the radiation back scattering and/or transmittance coefficients are two-dimensional, plain ones. In the majority of cases (except functional diagnostics of skin surface) it is also necessary to analyze the functional dynamic distribution as a function of depth of the area under investigation.

In the diffusely scattering media, biological tissues being among them for optical radiation of the near IR-range, contribution in the spatial-temporal distribution of transmittance and/or back scattering coefficients are different for different depth layers. Deep layers contribute in the transmittance and/or back scattering coefficients at spatial frequencies of about the same scale as the inverse depth of layers. Therefore, by subsequently filtering out higher and higher spatial frequencies, it is possible to separate dynamic maps the contribution of deeper and deeper layers.

Stroboscopic illumination, synchronous with different physiological rhythms of living organisms may be applied: cardiopulsation, breathing, metabolic, or thermoregulative ones. The stroboscopic illumination for different organism parts can be delayed in time, for example, for reaching maximal possible contrast during pulse wave visualization.

For estimation of distribution of physiological processes functional dynamics over the depth, multibeam illumination of the region investigated is used.

The distribution over the depth of the functional changes in concentration of physiological pigments is reflected by measuring the temporal dynamics of the radiation transmittance and/or back scattered coefficients in a radial distribution around the illuminating beam. The relative contribution of deeper back scattering layers is increased with increasing the distance from the beam. The is why the distribution over the depth is estimated by integral changes in the transmittance and/or back scattering coefficients as a function of the radius, r, the coefficient of the transmitted radiation, Ktr(r) and the coefficient of back scattered radiation, Kbsc(r), respectively, in the radial region of around the beam as a function of the radius. The procedure of normalization of transmitted and back scattered optical radiation intensity, taken as a function of r, by the intensity of the illuminating beam is performed during the calculation of Ktr(r) and Kbsc(r) which automatically suppresses the inhomogeneities in the transmittance of the surface layers and the illumination instabilities. By increasing the number of discrete points ( the number of independent elements of the photodetector surface) within the radial region around the beam, the reliability of separation of the dynamics of physiological parameters over the depth is increased by a factor or a cluster analysis. Under these conditions the signal/noise ratio for each discrete element is correspondingly decreased. These opposed modes are to be considered during the optimization procedure of the spatial resolution of the photodetector system. The distance between the beams is limited by the requirement of continuous registration of the dynamic images over the space of the investigated region: it must be much less than the functional dynamics spatial correlation length, or otherwise, about ten or more points of the dynamic imaging must be located at the correlated functional dynamics regions. Practically, the distance between the beams is optimized taking into consideration the two opposed modes—one for increasing the probing depth and the other for improving the spatial resolution.

It should be mentioned in addition, that as the distance from the illuminating beam is increasing, back scattered beams are coming from the larger depth, and the effective length L of their path through the light absorbing physiological pigments increases. For this reason, the modulation of the back scattered radiation also increases as the radius increases under the same functional variation of pigment concentration (C), oxyhemoglobin, for example. Actually, the modulation is determined by the amplitudes of the absorption changes which is proportional to CL. This is also is taken into account when the distance between illuminating beams during dynamic mapping procedure is optimized.

As a simplified variant, one illuminating beam is applied in some cases. This variant is sufficient for investigation of the functional dynamics over the depth, which is important, for example, for estimation of the tumor location depth etc. At the radius corresponding to the location depth of a tumor, a considerable change in the temporal behavior of the back scattering coefficient must be observed due to changes in the character of microcirculation functional dynamics and metabolism of the pathological tissues.

Besides, scanning of the investigated region by one or several beams is used. The scanning can considerably improve the spatial contrast, but it is necessary to work with increased intensities, since under these conditions the signal/noise ratio is decreased due to a decrease in registration time of a spatial element of the region investigated. By increasing the number of simultaneously scanning beams, the signal/noise ratio is correspondingly improved and the registration time decreased. Scanning time for obtaining one instant frame is chosen to be much less than the time constant of the investigated process or less than the interval between extrema observed in its dynamics. For each point of the investigated region, from the temporal sequences of such frames, changes in transparency and/or back scattering at the equidistant points arc chosen, thus obtaining radial spatial-temporal distribution of these coefficients. Using circular correlation of the temporal coefficients, dynamics of different radial scales, i.e. the distribution of the functional dynamics over the depth of the investigated region, can be investigated.

To extract the partial dynamic maps connected with microcirculation functioning and cell metabolism, spectral filters for investigation of selective absorption of oxyhemoglobin, deoxygenated hemoglobin and cytochrome aa3 are applied. In addition, spectral radiation selectivity in the above mentioned regions helps to exclude light scattering from the surface of the investigated region, which is only slightly wavelength dependent under the conditions of measurements of the back scattered radiation coming from the depth of the living organism. For separation of image dynamics connected with microcirculation functional dynamics, hemoglobin spectral absorption bands in the wavelength range from $0.38\mu$ to $0.48\mu$ and/or from $0.52\mu$ to $0.62\mu$ are chosen.

To obtain spatial-temporal dynamics of arterial and venous blood content and cell metabolism, differential frequency modulation of the wavelength of the electromagnetic radiation illuminating the surface of the living organism is used. The amplitude modulation of the dynamic maps is synchronously recorded at the modulation frequency and at double the one being performed. For the realization of maximal selectivity of the method, the wavelength about which the modulation is performed is chosen near the extremum and at the spectral intervals with maximal steepness. For example, to separate spatial-temporal dynamics of venous blood, the modulation wavelength interval from $0.6\mu$ to $0.75\mu$ is used, that for arterial blood—from $1.0\mu$ to $1.1\mu$ and for cytochrome aa3—from $0.85\mu$ to $0.9\mu$. More specifically, for separating venous blood distribution dynamics of oxyhemoglobin, deoxygenated hemoglobin and cytochrome aa3, the modulation is performed about the following wavelengths: $0.7\mu$—under these conditions the signal appears at the modulation frequency with the phase corresponding to an increase in the back scattering coefficient together with the wavelength increase (let take this as phase 0); $0.735\mu$—in this case the signal is observed at the doubled frequency with the phase, corresponding to a decrease in the back scattering coefficient with deviation from the extremum; $0.745\mu$ here the signal at the modulation frequency with the phase opposite to that of the signal at $0.7\mu$; $0.76\mu$—here the signal with the doubled frequency modulation and the phase opposite to that of $0.735\mu$ signal. The modulation on these wavelengths which are characteristic of venous blood content can be used both separately and simultaneously. In the latter case multichannel correlative detection is applied, which increases greatly the recognition potential of venous blood distribution.

For separation of partial dynamics of arterial blood distribution, the modulation is performed near the following wavelengths: $0.815\mu$, the signal at the modulation frequency with the phase p; from $0.95\mu$ to $1.3\mu$, the signal at the modulation frequency with the phase 0. The efficiency of separation of partial dynamics of the arterial blood distribution increases under the conditions of simultaneous modulation at two above described spectral ranges and the employment of the correlative detection via two channels.

To isolate partial dynamics of cell metabolism, the modulation at the wavelength near the absorption maximum of oxidized cytochrome aa3 at $0.825\mu$ wavelength is used. When the modulation amplitude is high enough, plus or minus $0.025\mu$, the signal is observed at the doubled modulation frequency with the phase corresponding to the increase in the back scattering coefficient with deviation from the extremum.

It must be stressed that, together with the spectral selection, to separate the signals from the deep tissues in the presence of radiation scattered from the surface, the time independence of scattered light is used, since radiation back scattered by deep tissues is time modulated by functional dynamics of microcirculation and the metabolism in them.

To reveal the functional synergy of the area investigated, the measured temporal sequences of image—the dynamic image—are transformed with the help of mathematical analysis (factor, cluster or any other type of functional analysis) into a single map with separated regions of high correlation level of the functional dynamics or those with similar parameters of such dynamics (if cross-correlation of the whole area is high). Inside of the separated regions functional behavior of living organism tissues is cross-correlated. Such a map is called a functional picture, a functional image or as is preferred, a functional map, and the corresponding procedure is called functional mapping.

As a distinctive parameter in the functional mapping, the coefficient of cross-correlation of temporal dynamics of transmittance and/or back scattering coefficients is calculated. It must be stressed that the characteristic cross-correlation length, in general, is different for different physiological processes, for different mechanisms of its regulation and varies with changes in the living organism state. Therefore, the same living organism or a part of it is described by several different mutually supplemental functional maps. A single or several functional maps are obtained as a result of analysis of tens and hundreds such maps included in the temporal sequence of dynamic mapping procedure.

Functional maps of the living system are superimposed on its morphological image, obtained, for example, with the help of tomography, thereby reflecting the spatial distribution of functional dynamics.

A principle distinction between functional mapping and traditional morphological mappings should be stressed. In the former case, one reveals and localizes the functional "landscape"—the details of the functional organization, that is, synergy of physiological dynamics of the area under investigation, while for the latter one the details of the spatial structure are of importance. As a rule, the characteristic dimension of the functional "landscape" (characteristic cross-correlation length) is much larger than the spatial sample size, therefore functional mapping at such a high spatial resolution is not necessary. Each physiological tissue system, microcirculation and metabolism, is described with each own peculiar set of functional maps.

It should also be mentioned that the functional maps, summarizing the results of tens or hundreds of dynamic map images, give the possibility of compactly storing information in a database, including a variety of early functional precursors of pathology. In this way a baseline of normal and pathological maps can be built up, allowing the functional maps to be interpreted against a database of normal versus pathological maps.

Different regions with a high internal cross-correlation at the functional map are distinguished by the character of temporal dynamics of the back scattering and/or transmittance coefficients. There may be periodical changes of the coefficient, reflecting physiological rhythms of different time constant, amplitude, delay or relaxation changes in the process of physiological reactions of different time constant and amplitude, initiated by redistribution of blood content and metabolism rate in the process of vital activity.

In these cases, when a physiological process presents a spreading wave, as a distinctive parameter during the procedure of functional imaging, the velocity of wave-like changes in back scattering and/or transmittance of electromagnetic radiation is used. For revealing such wave-like processes at the dynamic maps, a method of time delayed cross-correlation, the delay being linearly dependent on the coordinate and variable in length $d1/V$ (where $d1$ is spatial sample interval, and V—variable velocity), which is chosen to reach maximal cross-correlation. Such an approach is effective, for example, under the conditions of mapping of spreading depression waves in brain cortex. The velocity of these waves is very sensitive to changes in tissues, accompanying the development of tumors. In a similar way, the waves of blood content of hands can be mapped to reveal microcirculation disturbances.

As a distinctive parameters during separation of spatial regions, the frequency of temporal changes in transmittance and/or back scattering coefficients can be used, as well as time delay in the coefficients changing and the position of extrema of these coefficients.

Dynamic mapping of living organism is performed under different natural conditions: in sleeping and awaken states, before and after eating, etc. For each state its own set of functional maps is a characteristic which reflects microcirculation and metabolism dynamics. The aggregate of such functional maps for different states of living organisms, put into the data bank, gives a sufficiently complete description of the tissue functional status to reveal the earliest precursors of pathology under repeated investigation.

To separate the dynamically maps reflecting microcirculation functioning, especially in back scattered radiation in the presence of background scattering from the living organism surface, a synchronous signal accumulation at the frequencies of natural physiological rhythms is applied. As a source of reference signals, traditional electrophysiological sensors are used. This mode is used for separation of respiratory and cardiopulsation rhythms, or muscle microtremor. When natural respiratory rhythm is used as a synchronizing one, the functional maps reflect the distribution of respiratory pulsation amplitude and a delay (phase) of microcirculation blood content at the oxyhemoglobin absorption band in respect to the amplitude and phase of the respiratory rhythm. The living organism tissue functional state is reflected also in the dynamic maps of the relative amplitude and phase distribution of the respiratory rhythm at the spectral absorption band of cytochrome aa3, characterizing the cell metabolism state. The dynamic maps of such a fast functional dynamics reflect, for the first time, the state of a regulation nerve control of the microcirculation and reveal the earliest signs of its disturbance.

The most effective mode for the dynamic microcirculation mapping is synchronous signal accumulation at the cardiopulsation frequency. As a reference signal, that of the photoplethismogram could conveniently be used, at the finger tip, for example. Variation in such registration delay (phase) depends, in principle, on the coordinates of the living organism's surface at which the photoplethismogram is measured. The velocity of the pulse wave can be estimated via this dependence.

The modulation amplitude of the tissue blood content by microtremor is very small, and the rhythm is expressed only slightly, making the signal noise-like. However, when the muscles are strained, this rhythm becomes more pronounced and its amplitude noticeably increases. The amplitude of such a modulation characterizes the state of the muscle tissue. This is an optical mode of tremor visualization. The modulation of blood content by microtremor characterizes an active reverse action of the muscle on its blood supply, especially venous out flow.

In functional imaging, contrary to the morphological one, it is necessary to investigate functionally connected regions simultaneously. Only in such a way it is possible to reveal the character of the functional synergy not only between different regions, motor brain cortex and skeletal muscles for example, or internal organs and the dermatomes by the nervous system connected with them such as Zakharjin-Ged skin zones. Of special importance in the investigation of paired organs is the simultaneous functional mapping of both organs. For example, hands and feet actively participate in thermoregulation and, therefore, are highly saturated with arterial-venous anastomosis. So, when the conductivity of nervous links is disturbed (e.g. at multiple sclerosis) a time delay of the functional dynamics is observed at hands and feet. Simultaneous mapping is also very important for the investigation of mammary glands. An asymmetry in the functional maps with different time scales of such organs may indicate the disturbance of nervous and/or humoral regulation including tumor appearance.

Valuable information is obtained via dynamic mapping of physiological reactions of living organism when some external influences are applied. With the help of the corresponding choice of the influences the contribution of different physiological systems could be accented. For example, variation of the temperature of the environment initiates thermoregulation reactions of microcirculation in skin. Furthermore, short time physical exercising tests the muscles microcirculation state, while more prolong exercising tests the cell metabolism functional state in muscles; reflective influences (pain, emotions, etc.) reveal the state of nervous regulation; changes in the composition of air indicate the oxygenation tissue status. Different functional states of living organism are differentiated by the spatial-temporal organization of the optical dynamic maps, reflecting transient processes of the tissue physiological reactions. Depending on the state of living organism, different types of such processes are observed: relaxation, oscillation, or wave like ones. Taking into consideration that each type of the transition processes is described by a set of quantitative parameters (amplitudes, relaxation times, periods, phases, delays etc.) and also that optical dynamic maps are registered simultaneously at several spectral ranges (in order to characterize the behavior of different physiological pigments), optical functional imaging has a great potential for recognition of the earliest pathological changes in the functional state of living organism.

It is important that the chosen external influences are close to the natural ones, i.e. ones that the living organism has been adapted to in the course of evolution: namely those connected with breathing, taking food, physical exercises, thermoregulation, and nervous reactions. Two types of the functional maps are investigated. The first one characterizes physiological reactions of living organism tissues on relatively small (differential) external influences, e.g. light physical exercises, changes in the composition of breathed in air, external temperature within the comfortable range, etc. Such functional maps characterize the functional organization and the state of the tissue physiological systems within the limits of its natural comfortable physiological reactions. The structure of these functional maps is practically independent of the amplitude of external influence, such dependence is observed only for the amplitude changes of the radiation transmittance and/or back scattering coefficients at the dynamic maps.

The second type of functional maps is obtained for sufficiently large external influences intensities, when the structure of the functional maps changes. The intensities of external influences at which such changes appear characterize the dynamic ranges of the physiological reactions of living organism tissues, and therefore, such maps reflect the whole-organism stability of the living system. As natural external influences, changing of external physical conditions is used: temperature, humidity, external electrical field, vibrations and others.

Changes in temperature, thermal flows, and humidity which control the evaporation rate from the living organism surface initiate physiological reactions of the thermoregulation system which are provided, primarily, by skin microcirculation functioning. Under these conditions, functional state of skin microcirculation network is reflected at the corresponding dynamic and functional maps.

Functional state of living organism tissues is determined by their oxygenation, which depends on the parameters of external breathing: its frequency, depth, and the ratio between the inhalation and exhalation length. For this reason these parameters are used as external influences during the functional mapping of living organism. Both fast temporal dynamics with the time constant of less than one minute, and more slow humoral one are observed under these conditions. The fast one is observed, for example, at breath holding. The time of recovery of the tissue parameters after breaking off the external influence characterizes total stability of the organism's homeostasis: the shorter this time, the higher organism stability.

One of the strongest natural external influences is a change in the composition of air breathed in . For this purpose both enriched oxygen mixtures, and oxygen deficient or enriched with CO2 and/or nitrogen mixtures are used. Under these conditions, a characteristic redistribution of the values of optical radiation transparency and/or back scattering coefficients in the spectral bands of oxy-, deoxy-hemoglobin and cytochrome aa3 is observed. The earliest stages of obstruction (lung deficiency) are seen both as peculiarities in the spatial-temporal distribution of the above mentioned coefficients, and as an increase in the recovery time after cessation of the influence action.

Vibration, applied as an external influence, reveals in the dynamic maps the functional reactivity of microcirculation connected with mechanoreception. Dynamic and functional maps of living organism microcirculation reactions depend on the vibration influence frequency, in accordance with the frequency dependence of mechanoreceptors. In such maps, the regions with abnormal temporal dynamics of the optical radiation transmittance and/or back scattering coefficients at the spectral absorption bands of oxy- and deoxyhemoglobin are seen as higher contrast ones, as compared with the surrounding tissues and with statistically averaged data. Changes in microcirculation also initiate corresponding reactions in cell metabolism which are reflected at the dynamically maps of optical radiation transmittance and/or back scattering coefficients at the absorption band of cytochrome aa3.

The comparison of these two types of dynamic functional maps permits the estimation of the perfusion state. Under the conditions of frequency variable vibrational influence, dynamic maps at the cytochrome aa3 absorption band reflect also the characteristic frequency dependence (frequency range from 8 to 30 Hz) of the cell metabolism rate.

An electric field, taken as an external influence, affect the nonspecific skin reception and reflexively provoke microcirculation skin network reaction. Skin microcirculation has been found to "mark" external electric fields, constant and alternating ones, beginning with relatively small ones of about 1000 V/cm. This sensitivity depends significantly on the voltage distribution across living organism surface, as well as on the average frequency, the character of its temporal variability and the length of time acted upon.

The functional maps, obtained under physical exercise conditions, reflect primarily the state of working muscle tissues. At first, they reflect the character of metabolic resource utilization, then (after 10–20 s) changes in microcirculation are added as well as associated processes of metabolic support of energy losses in muscles. In this way metabolic resources are estimated, via a measure of the time delay in the functional maps, as well as the possibility of measuring the microcirculation supply of the muscles, the perfusion state and cell metabolism. It worth noting that under physical exercise of one of two muscle pairs, a physiological reaction is observed also for the other one, and, in addition, practically the whole muscle system responds. The functional map of the lattter system reflects the character of a reflective connection between the muscles and also humoral reactions.

Ultrasound, as an external influence, also permits examination of internal organs and tissues, but with much higher spatial directionality. By scanning an organ with ultrasound beam, pathologies can be revealed and localized via the anomalies appearing in the functional maps of the referent dermatomes.

When an alternating magnetic field with the frequency of tens to hundreds kilohertz, for which biological tissues are transparent, is applied as an external influence (in the form of exciting currents), it initiates reaction of the internal organs: liver, kidney and other organs. Under these conditions, the reflective and humoral projections (Zakharjin-Ged skin zones) of the affected organs are revealed at the functional maps of the skin tissues reflecting both the state of these organs and their connection with the referent dermatomes.

A living organism's tissue functional state is clearly revealed by the functional maps under the application of external pressure. Under these conditions, changes in both blood content and rheological characteristics of tissues are observed as a result of changes in correlation of the radiation scattering inhomogeneities. The changes in blood content and tissue rheology can be separated, taking into consideration the fact that blood content changes are spectrally dependent, while Theological ones practically are not. The most informative are functional maps, reflecting transient processes of tissue physiological reactions on a jump-like pressure application and removal. The jump-like pressure application and removal means that the corresponding time must be much less than the time interval of transient physiological reaction in answer to pressure application and removal. A choice of time interval between pressure application and removal is also important: it must be larger than that of establishing of the tissues stationary physiological state after pressure application. Time of establishing of physiological tissue status after pressure application and removal is of separate diagnostic significance. This time is taken to be equal to that of reaching of its initial stationary physiological pigment concentration level with an accuracy of 10%. Investigation of continuous spatial distribution of the continuous temporal changes in the radiation transmittance and/or back scattering coefficients, when using pressure as an external influence, reveals regions with disturbed microcirculation functional dynamics: with amplitude deviation from normal state, the time constant of physiological reactions is proportional to the recovery times of the stationary physiological tissue status after physiological reactions. Pressure, as external influence, effectively reveals mammary gland inhomogeneities, including the early stages of cancer.

Thermal flows of about 1 mW per square centimeter affect noticeably non-sensible perspiration rate, as one of the main living organism thermoregulation mechanisms. Skin microcirculation is also changed under these conditions. For this reason, it is quite natural to use such thermal flows as an external influence for organism functional mapping. The intensity of the affecting thermal flow is time varied and redistributed across the living organism surface. The functional maps of living organisms are studied as a function of the stimulus spatial-temporal organization, e.g. under the influence of this stimulus on one of the hands or feet. The most informative are the functional maps reflecting the reactions on fast (as compared with the reversed reaction time) switching on/switching off of thermal flow redistribution. In particular, instead of a heating flow, a cooling one can be used: it is enough for this purpose to place near the living organism a surface having the temperature below that of the environment.

BEST MODE FOR CARRYING OUT THE INVENTION

In accordance with FIG. 1, living organism surface 1 is illuminated with a source 2 of optical radiation. The spatial distribution of the intensity of transmitted and/or back scattered radiation is converted respectively by detectors 3 and 4 of scattered radiation into electrical signals, coming to the corresponding inputs of a commutator 5. As detectors 3, 4 of the scattered radiation, a video camera based on a charge-coupled device can be used, since it is characterized by sufficient spatial resolution and sensitivity at the near IR-range. Commutator 5 transfers sequentially and alternatively, for example, through one frame, signals from the outputs of detectors 3 and 4 to the analog-to-digital converter 6. Digital signals via input/output controller 7 comes the computer system 8, where is stored in memory unit 9 as map sequences, which can be displayed, with the help of processor 10 and display controller 11, at display monitor 12. To extend the dynamic range, processor 10 may put the corresponding color in accordance with a definite range of the signal level.

The temporal map sequences thus obtained are mathematically treated, i.e. analyzed with factor, cluster and/or other type of functional analysis. Such treatment converts a temporal map sequence into a single map, separating the regions with a high level of the functional dynamics correlation or with proximity of such dynamics parameters. As a distinctive parameter, the cross-correlation coefficient of temporal dynamics of the transmittance and/or back scattering coefficients can be used for separation of the interconnected regions. In this case, mathematical treatment at the processor system calculates the cross-correlation functions between temporal dependencies of the transmittance and/ or back scattering coefficients, relating to the map separate spatial points A group of points with maxima of the cross-correlation functions differing by not more than some definite value are united into a single region and are marked by the same color when displayed at the monitor. The other group of points, also satisfying to the aforementioned requirement, are marked by the other color and so forth. Due to such procedures the temporal sequence of spatial maps is converted into a single functional map or functional image. This mathematical treatment provides a good separation of slowly changing signals in the presence of background noise which were not seen at the initial maps.

Input-output controller 7 may contain one of several known controllers, securing information input and output from the computer system 8. Into the input/output controller 7 analog-to-digital converters are included, their number being equal to the number of the analog outputs destined for transformation into digital codes.

Input/output controller 7 transfers synchronized scanning signals and the signal of charge transfer control from the section accumulating radiation scattered by living organism into the detectors 3 and 4 (for the case using video camera based on charge-coupled devices). The latter signal permits changing accumulation time at the target by a software, thereby increasing the signal/noise ratio. Input/output controller 7 also controls switching of commutator 5, including, for example a counter trigger. A commutator controlled by a digital code may also be used, but in this case, a meter is set up at the commutator input (this meter is included into commutator 5). In a general case, several control signals are brought to scattered radiation detectors 3, 4 and to commutator 5, for this reason the corresponding connections are shown as busses.

Figure 2:
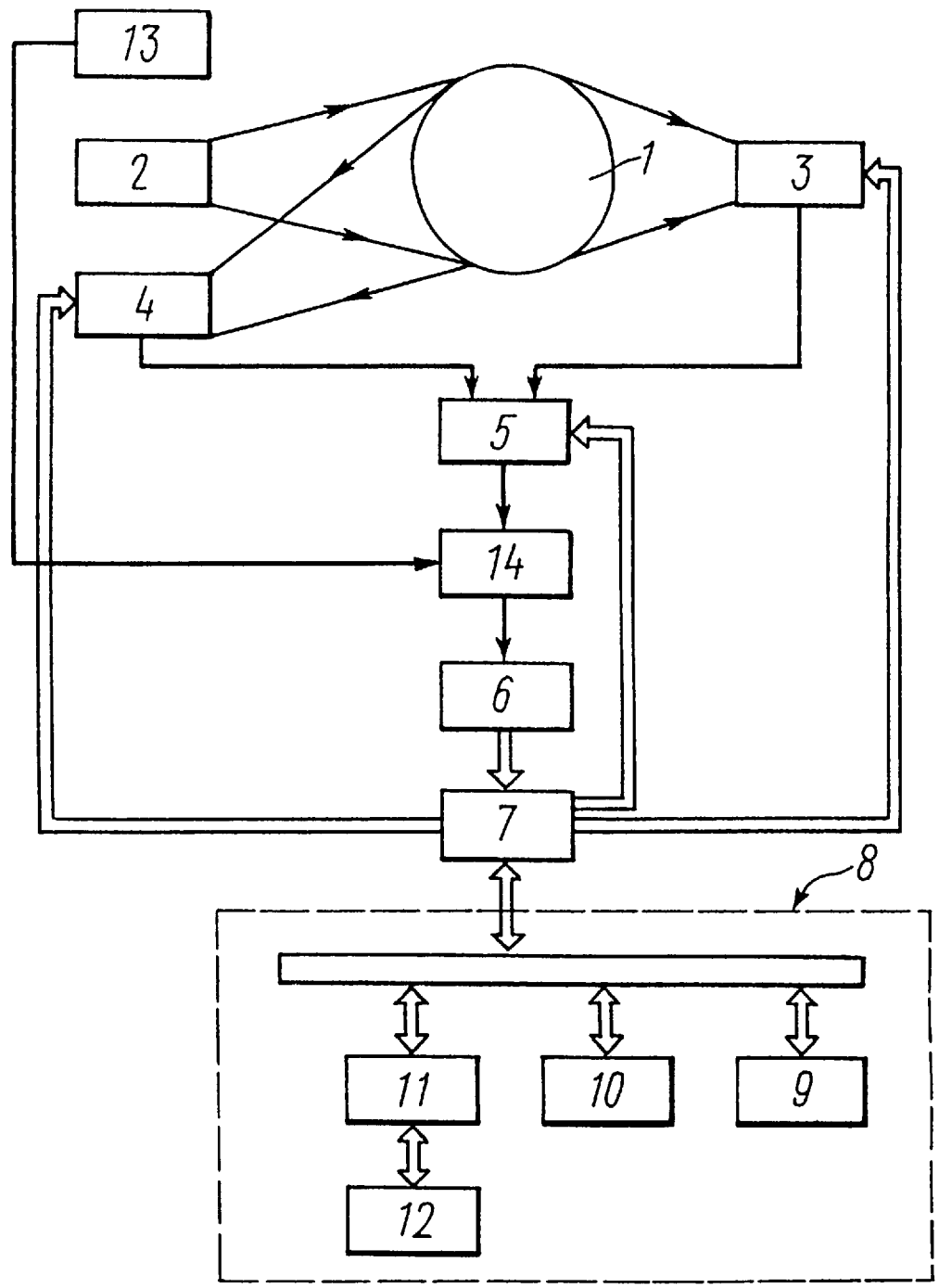
FIG. 2 is a general diagram of a variant of a set-up for the investigation of functional dynamics of living organism physiological processes with normalization of the intensity of detected radiation, according to the invention.

To avoid temporal instability of source 2 of optical radiation and inhomogeneities in the distribution of illuminating intensity, the apparatus contains additionally (FIG. 2) referent detector 13, optically connected with source 2 of optical radiation, output of which is connected with divisor 14, inserted between commutator 5 output and analog-to-digital converter 6.

Figure 3:
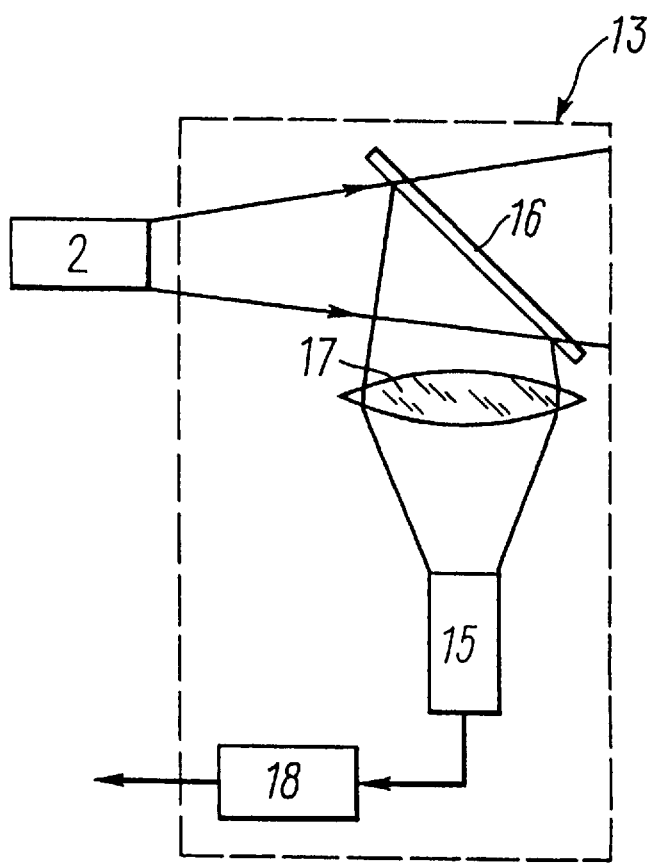
FIG. 3 is a diagram of one of the possible construction variants of the referent detector.

One of the possible variants of the reference detector realization is shown in FIG. 3. The reference detector 13 may include a photodetector 15, optically connected via semitransparent plate 16 and lens 17 with source 2 of the optical radiation. Light is reflected from semitransparent plate 16 and is focused by lens 17 to photodetector 15, where it is converted to the electric signal and amplified by amplifier 18.

The transmittance band of amplifier 18 is chosen to be proportional to the inverse value of the signal accumulation time at detectors of scattered by living organism radiation. The output signal of amplifier 18 is proportional to the radiation intensity, coming to the living organism, and is received by divisor 14, normalizing the output signal of detectors 3, 4 of radiation scattered by the living organism. An amplifier with controlled amplifying coefficient, widely used at set-ups of automatic amplifier control, may be used as divisor 14.

It is worth noting that, in most cases, to diagnose a living organism's functional state, not absolute values of coefficients K of transmittance and back scattering of the optical radiation are of importance, but only their relative changes in time, $DK/K=DI/I$, where I is the intensity of transmitted or back scattered radiation. This relative value is practically independent of the illumination inhomogeneity and temporal instability, under the condition that interframe interval is less than the characteristic time of the illumination instability. In such a case, reference detector 13 and divisor 14 may not be necessary.

As mentioned above, to separate the dynamic maps, reflecting microcirculation functioning, under the conditions of insufficient illumination stability and without proper control of living organism surface 1 movements during measurements, a stroboscopic pulse illumination, synchronized with one of the natural living organism's physiological rhythms (breathing, cardiopulsation etc.), modulating microcirculation, is used. For this purpose, the apparatus (FIG. 4) contains a sensor 19 of natural physiological rhythm, which could be realized, depending on the concrete task, via known and widely used in medical practice, meters of breathing rhythm as well as of cardiopulsations and muscle tremor.

The output signal from sensor 19 of physiological rhythm is received by temporal modulator 20. This modulator may be realized according to scheme of FIG. 5. It contains a sequentially connected Schmitt trigger 21, delay generator 22 and generator 23 of the modulating pulse. Consider the functioning of the temporal generator when a pulse wave is presented to its input. A rectangular pulse with a fast rise time is formed by a Schmitt trigger from the initial pulse signal. Generator 22 of delay forms a pulse whose leading edge is connected with that of the signal from the Schmitt trigger output and whose duration is determined by a necessary delay. This pulse signal comes to generator 23 of modulating pulse input, where a pulse is formed, the leading edge being connected with the leading edge of the input signal and the duration being determined by the task under investigation, as a rule, not longer than several percent of the pulse signal period. The pulse signal from temporal modulator 20 comes to source 2 of optical radiation and to input-output controller 7. Source 2 of optical radiation operates only during pulse signal duration. Bringing the signal from modulator 20 output to input-output controller 7 is necessary for synchronization of the process of digitizing the signal from detectors 3,4 of the scattered radiation.

For the case when a video camera based on charge-coupled devices are used as detectors 3, 4 of scattered radiation, the synchronization is carried out in such a way that charge transfer from the accumulative section to the storage section proceeds just after the termination of the pulse signal of the temporal modulator 20.

Figure 4:
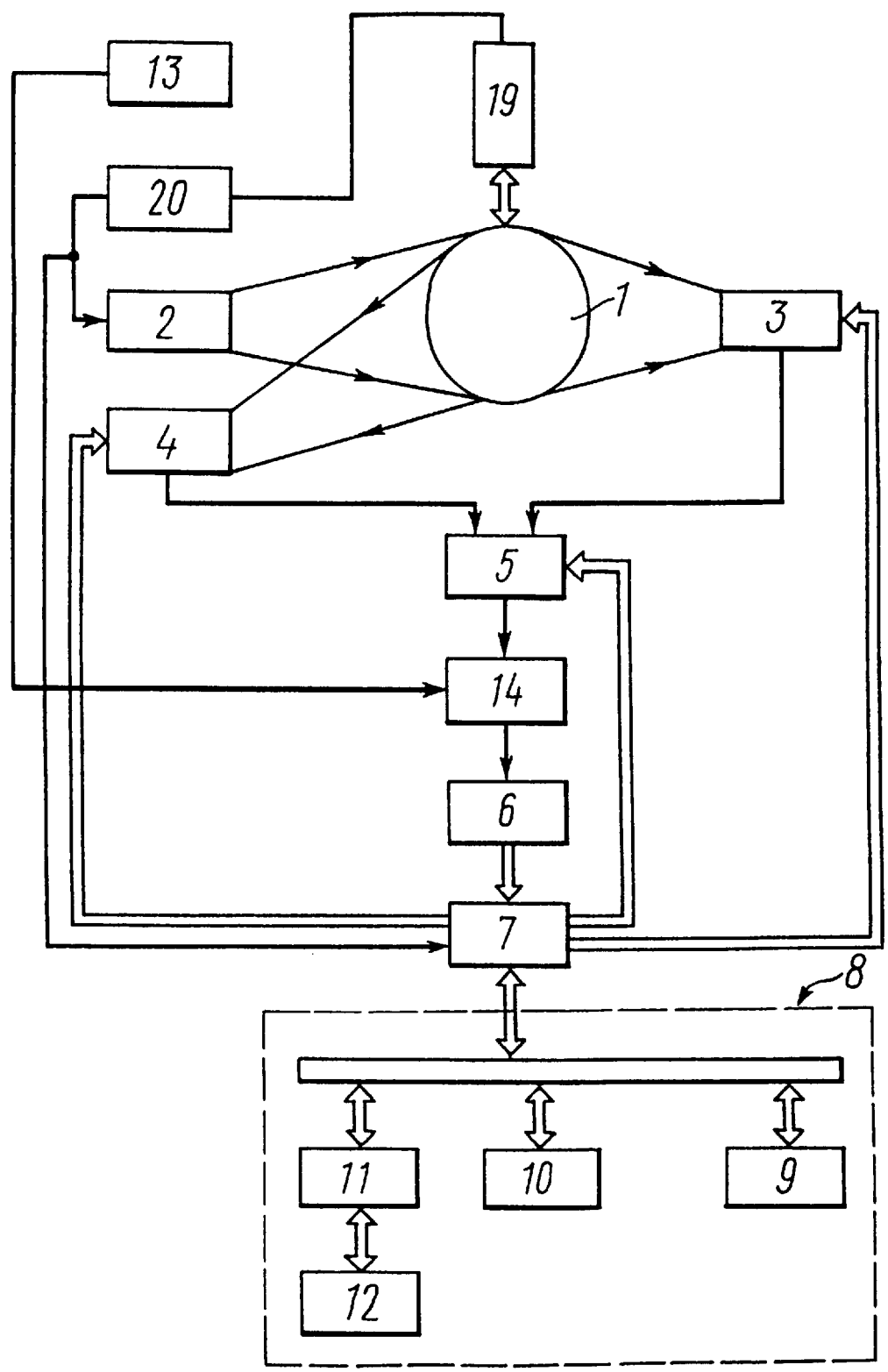
FIG. 4 is a general block diagram of a variant of a set-up for the investigation of functional dynamics of living organism physiological processes with synchronization from the natural living organism physiological rhythms, according to the invention.
Figures 5, 6:
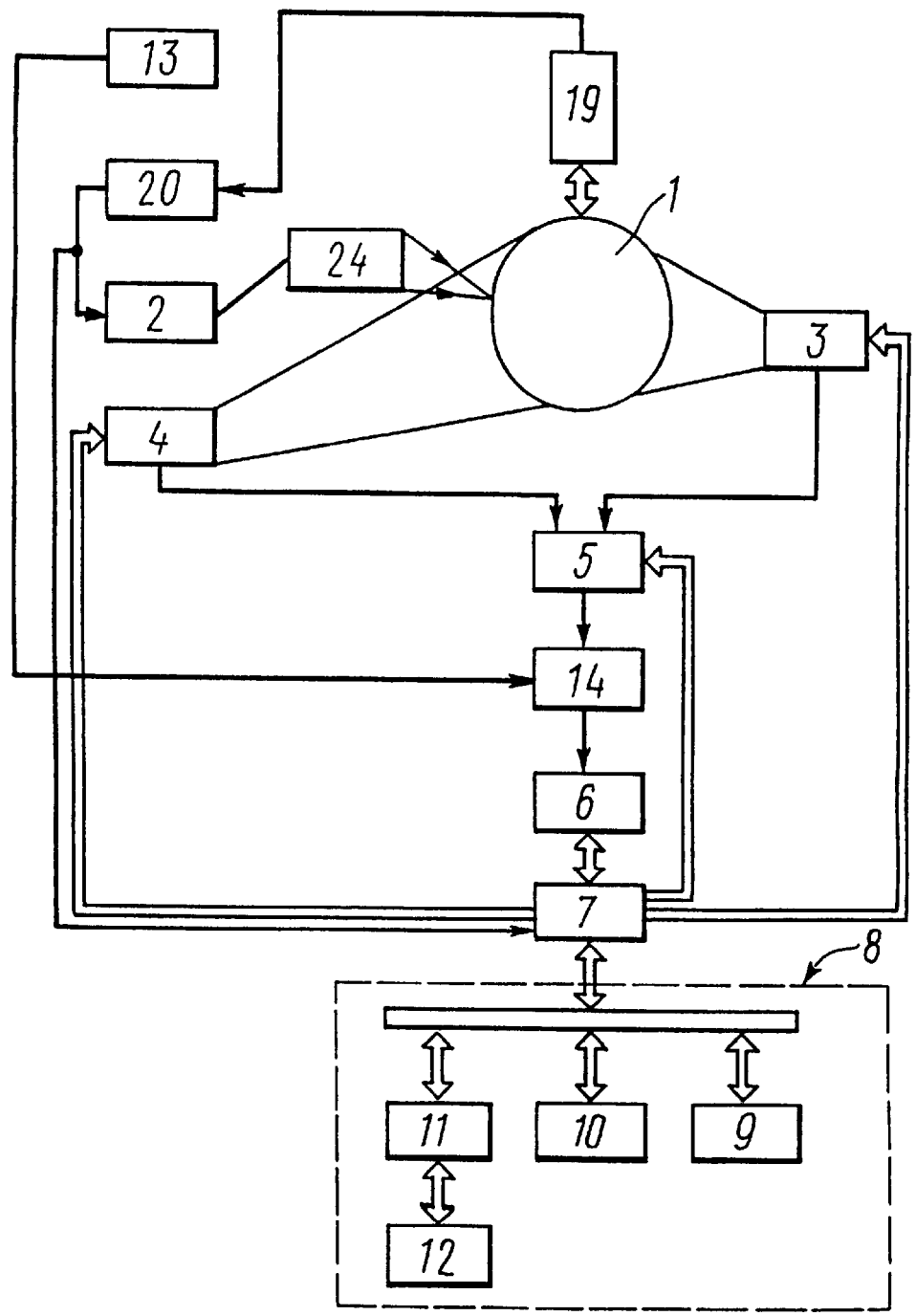
FIG. 5 is a diagram of one of the possible variants of the temporal modulator.
FIG. 6 is a general block diagram of a set-up for investigation of functional dynamics of living organism physiological processes employing optical radiation focusing into separate points at the living organism surface, according to the invention.

The variant of the apparatus shown in FIGS. 4 and 5 may be used also for separation of the dynamic maps of the back-scattered radiation, reflecting microcirculation functioning recorded with detector 4. This is especially useful to eliminate the presence of background scattering from the surface of living organism not containing blood vessels layers, and under continuous illumination. In this case, the synchronizing signal from sensor 19 of the natural rhythm through temporal modulator 20 is brought only to input-output controller 7 for digitizing of signals of detectors 3,4 and for the synchronous frame accumulation into memory unit 9 of computer system 8.

For separation of the dynamic maps characterizing living organism tissues located at different depths, the illuminating radiation is focused at least at one surface point and a radial distribution of the light scattered around the beam is registered. To provide such focusing of optical radiation, optical system 24 (FIG. 6) is included between the source of optical radiation and living organism. In the simplest case of radiation focusing to one point the optical system may be represented by a zoom lens.

To obtain several focused beams, an optical system, shown in FIG. 7, may be used. It consists of disk 25, placed in the plane of the aperture of the optical radiation source, fiberoptic cables 26 being fixed in it. The number of fiberoptic cables 26 is determined by the number of points at living organism surface the radiation is focused on. The other ends of fiberoptic cables 26 are fixed at the surface of the other disk 27 at some distance from each other, which is determined by mutual disposition of the necessary points at the surface of living organism. The images of the fiberoptic cable outputs are projected onto the living organism surface with the help of zoom lens 28.

For scanning of the illuminated points at the living organism surface, a scanning system 29 (FIG. 8 and 9) is included between the optical system and this surface. The scanning system consists of driver 30, scanning control block 31, galvanometer 32 and mirror 33. The latter is located at the optical axis of the optical system 24 and is mechanically connected via galvanometer 32 with driver 30, which is connected with the output of scanning control block 31. The most purposeful is usage of discrete beam (set of beams) capable of shifting across the surface of living organism.

In this case, a stepwise driver may be used as driver 30; and to turn it by one step, the corresponding pulse voltages are brought at the stepwise driver from scanning control block 31. To synchronize the scanning process with the functioning of the apparatus as whole, and with detectors 3, 4 of scattered radiation, in particular, the control input of the scanning controlling block 31, is connected with the corresponding output of input-output controller 7.

In order to separate the partial image dynamics connected with microcirculation and cell metabolism, it is necessary to perform spectral filtration of the illuminating radiation and/or that of the transmitted and/or back scattered radiation. To accomplish this, at least one optical filter 34 is placed (FIG. 10) near the aperture of optical radiation source 2 and/or near detectors 3, 4 of scattered radiation.

Figure 11:
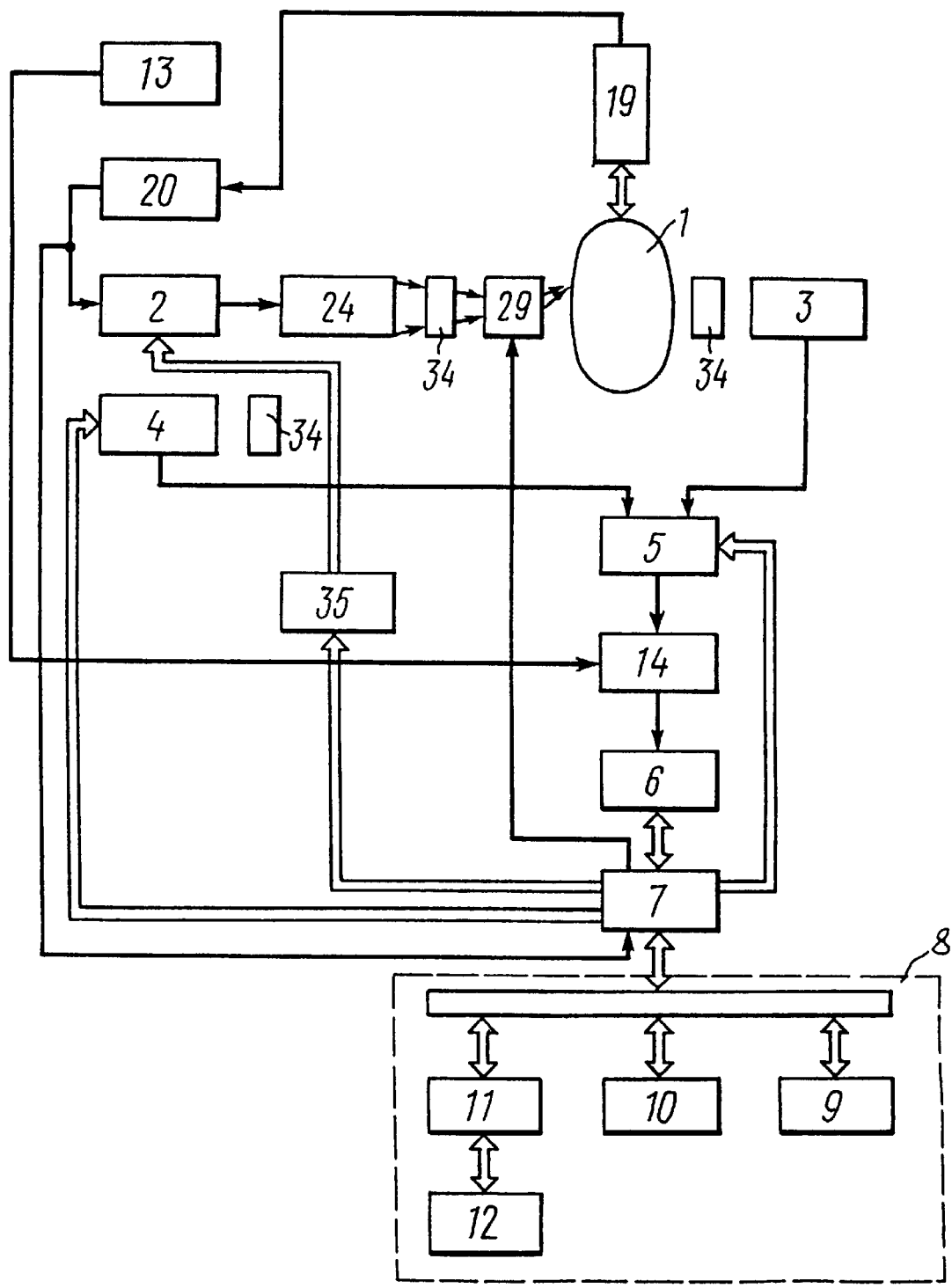
FIG. 11 is a general block diagram of a variant of a set-up for investigation of functional dynamics of living organism physiological processes with frequency modulation of optical radiation, according to the invention.

As mentioned above, the frequency modulation of radiation illuminating living organism, gives the possibility of obtaining partial dynamic maps, characterizing separately the functional dynamics of oxy-, deoxyhemoglobin and cytochrome aa3 concentration changes. For this purpose, the apparatus contains a frequency modulator 35, connected with source 2 of optical radiation (FIG. 11). In one of the possible apparatus variants, the frequency modulator can be realized as a set of controlled current sources. Each of the controlled current sources provides energy supply for one or several groups of light emitting diodes, located at optical radiation source 2. Each group of the diodes radiates light of each own wavelength.

Changes in optical radiation wavelength are provided by sequential switching of corresponding controlled current sources. The control signals come to the frequency modulator from the corresponding output of input-output controller 7.

The above described apparatus for diagnostics of living organism functional state as well as the prototype contains a source of optical radiation, a detector of transmitted radiation which is located at the opposite side from the illuminated part of living organism, sequentially connected to an analog-to-digital converter, an input-output controller and a computer system. It contains an additional detector of back scattered radiation, located at the same side of living organism as the radiation source and a commutator, which permits sequential acquisition, connecting to the analog-to-digital converter and to the subsequent recording tract, signals from both detectors of transmitted and back scattered radiation. Such two-channel registration of scattered radiation gives the possibility to sufficiently improve spatial resolution to reveal pathological tissue inhomogeneities, tumors for example, which are located near the illuminated surface, and also those which are located deep within both surfaces of living organism. However, the main advantage of the apparatus is that it works in a quite different regime: instead of only spatial distribution (one frame) as in the prototype, in this apparatus, with the help of analog-to-digital converter and input/output controller in the memory unit of the computer system, accumulates a continuous sequence of frames. To secure continuous registration in time, with the help of a computer via an input-output controller the intervals between the frames are set to be much less than the time constant of physiological process investigated. The commutator permits the acquisition of both the transmitted and back scattered radiation alternatively, thereby achieving practically simultaneous recording of scattered light from both sides. Such dynamic living organism image recording permits, as aforementioned, revealing the early stages of pathologies, including cancer tumors, since before a tumor achieves the size enough to be distinguished by single frame morphological mapping it may change sufficiently the character of functional dynamics of blood content microcirculation at much more extensive region of the living organism. This may be revealed by dynamic maps of living organism both under its natural variability and, especially, under the reactions on various external influences.

The method and the apparatus are absolutely harmless and give the possibility of obtaining functional images of a living organism, reflecting varied spatial-temporal organizations of physiological reactions of microcirculation and cell metabolism, which permits various disturbances in physiological regulation to be revealed at their earliest stages.

What is claimed is:

1. An apparatus for diagnostics of a living organism, organ or tissue, comprising:

a source of optical radiation of predetermined intensity providing a beam of said optical radiation having a wavelength range from 0.3 to 2.0 μm for illuminating a preselected portion of said living organism;

means optically aligned with a portion of said living organism opposite said preselected portion for detecting the intensity of said radiation transmitted through said living organism and providing a signal representative thereof;

means optically aligned adjacent said portion of said living organism for detecting the intensity of said radiation backscattered therefrom and providing a signal representative thereof;

an interface system including:
means operably connected to both of said detecting means for receiving said signals therefrom and providing sequential analog signals for processing,
means operably connected to said means for receiving said signals from said detecting means for converting said analog signals to digital signals,
an input/output controller operably connected to said converting means, said input/output controller including means for receiving said digital signals for transfer to a computer system and for receiving information from said computer system for transfer of said information back to both of said detecting means; and said computer system operably connected to said interface system, said computer system including means for receiving said digital signals, providing a temporal sequence of spatial maps, and converting said temporal sequence of spatial maps into at least one dynamic functional map representing spatial distribution of temporal changes to provide diagnostic information about functional conditions and synergy of physiological dynamics of said living organism under diagnosis.

2. The apparatus as defined in claims 1 further comprising means interconnected between said source and said interface system to substantially eliminate any temporal instability and inhomogeneities in the intensity of said source.

3. The apparatus as defined in claim 2 wherein said means interconnected between said source and said interface system to substantially eliminate any temporal instability and inhomogeneities in the intensity of said source comprises a beam splitter interposed between said source and said preselected portion of said living organism, a photodetector and an amplifier.

4. The apparatus as defined in claim 1 further comprising a sensor system operably interconnected to said source and said interface system, said sensor system including means adjacent said living organism for sensing at least one natural physiological rhythm of said living organism.

5. The apparatus as defined in claim 4 wherein one of said natural physiological rhythms of said living organism is its respiration rhythm.

6. The apparatus as defined in claim 4 wherein one of said natural physiological rhythms of said living organism is its cardiopulsation rhythm.

7. The apparatus as defined in claim 4 wherein one of said natural physiological rhythms of said living organism is its muscle tremor rhythm.

8. The apparatus as defined in claim 1 further comprising means for stroboscopically controlling said source to synchronize said beam output therefrom with a different one of said natural physiological rhythms of said living organism.

9. The apparatus as defined in claim 1 further comprising means interposed between said source and said living organism for focusing said beam to at least one preselected point on said preselected portion.

10. The apparatus as defined in claim 1 further comprising means interposed between said source and said living organism for scanning said beam to a preselected number of points on said preselected portion.

11. The apparatus as defined in claim 1 further comprising means interposed between said source and said portion for spectrally filtering said beam of radiation.

12. The apparatus as defined in claim 1 further comprising means connected to said source for frequency modulating said source.

13. An apparatus for diagnostics of a living organism, comprising:
a source of optical radiation of predetermined intensity providing a beam of said optical radiation having a preselected wavelength range for illuminating a preselected portion of said living organism;

means optically aligned with a portion of said living organism opposite said preselected portion for detecting the intensity of said radiation transmitted through said living organism and providing a signal representative thereof;

means optically aligned adjacent said portion of said living organism for detecting the intensity of said radiation backscattered therefrom and providing a signal representative thereof;

an interface system including:
means operably connected to both of said detecting means for receiving said signals therefrom and providing sequential analog signals for processing,
means operably connected to said means for receiving said signals from said detecting means for converting said analog signals to digital signals,
an input/output controller operably connected to said converting means, said input/output controller including means for receiving said digital signals for transfer to a computer system and receiving information from said computer system for transfer of said information back to both of said detecting means;

a sensor system operably interconnected with said source and said interface system, said sensor system including means adjacent said living organism for sensing at least one natural physiological rhythm of said living organism;

said computer system operably connected to said interface system, said computer system including means for receiving said digital signals, providing a temporal sequence of spatial maps, and converting said temporal sequence of spatial maps into at least one dynamic functional map representing spatial distribution of temporal changes to provide diagnostic information about functional conditions and synergy of physiological dynamics of said living organism under diagnosis.

14. The apparatus as defined in claim 13 further comprising means for stroboscopically controlling said source to synchronize said beam output therefrom with a different one of said natural physiological rhythms of said living organism.

15. A method of diagnostics of a living organism, comprising the steps of:
illuminating a preselected portion of said living organism with a beam of optical radiation having a wavelength range from 0.3 to 2.0 μm;
detecting backscattered radiation from said preselected portion and detecting transmitted radiation through said living organism;

continuously recording information obtained by detecting said backscattered and transmitted radiation;

providing a temporal sequence of spatial maps based on said recorded information; and converting said temporal sequence of spatial maps into at least one dynamic functional map representing spatial distribution of temporal changes to provide diagnostic information about functional conditions and synergy of physiological dynamics of said living organism under diagnosis.

16. The method as defined in claim 15 further comprising the step of selecting as said preselected portion of said living organism a skin area physiologically connected with an internal organ.

17. The method as defined in claim 16 further comprising the step of sensing at least one natural physiological rhythm of said living organism.

18. The method as defined in claim 17 further comprising the step of modulating by amplitude said beam of optical radiation synchronously with said at least one natural physiological rhythm of said living organism.

19. The method as defined in claim 17 wherein one of said natural physiological rhythms of said living organism is its respiration rhythm.

20. The method as defined in claim 17 wherein one of said natural physiological rhythms of said living organism is its cardiopulsation rhythm.

21. The method as defined in claim 17 wherein one of said natural physiological rhythms of said living organism is its muscle tremor rhythm.

22. The method as defined in claim 15 further comprising the step of modulating amplitude and/or frequency of said beam of optical radiation.

23. The method as defined in claim 15 further comprising the steps of concentrating said beam of radiation at a point on said portion of said living organism; and recording and analyzing temporal variations of radial distribution of said backscattered radiation around said beam.

24. The method as defined in claim 15 further comprising the step of spectral filtering said beam of radiation.

25. The method as defined in claim 15 further comprising the steps of:

detecting spatial regions in sequentially recorded spatial distributions which are distinct from each other by at least one parameter;

characterizing their temporal change; and recording and aggregating said spatial regions in the form of said dynamic functional map.

26. The method as defined in claim 25 further comprising the step of using as a distinctive parameter the cross correlation coefficient of said at least one parameter.

27. The method as defined in claim 25 further comprising the step of using as a distinctive parameter the velocity of temporal wave-like changes of said at least one parameter.

28. The method as defined in claim 25 further comprising the step of using as a distinctive parameter a frequency of temporal wave-like changes of said at least one parameter.

29. The method as defined in claim 25 further comprising the step of using as a distinctive parameter a temporal delay of changes of said at least one parameter.

30. The method as defined in claim 25 further comprising the step of using as a distinctive parameter a the number and position of extrema at temporal dynamics of said at least one parameter.

31. The method as defined in claim 25 wherein said recording step occurs synchronously with at least one natural physiological rhythm of said living organism.

32. The method as defined in claim 31 wherein one of said natural physiological rhythms of said living organism is its respiration rhythm.

33. The method as defined in claim 31 wherein one of said natural physiological rhythms of said living organism is its cardiopulsation rhythm.

34. The method as defined in claim 31 wherein one of said natural physiological rhythms of said living organism is its muscle tremor rhythm.

35. The method as defined in claim 15 further comprising the step of applying at least one external condition to said living organism.

36. The method as defined in claim 35 wherein vibration constitutes said external condition.

37. The method as defined in claim 36 further comprising the step of varying the frequency of said vibration.

38. The method as defined in claim 36 wherein an electric field constitutes said external condition.

39. The method as defined in claim 36 wherein a magnetic field constitutes said external condition.

40. The method of as defined in claim 39 further comprising the step of concentrating said magnetic field in an internal organ under diagnosis.

41. The method as defined in claim 35 wherein physical exercise constitutes said external condition.

42. The method as defined in claim 35 wherein ultrasound constitutes said external condition.

43. The method as defined in claim 42 further comprising the step of scanning an internal organ or deep tissue under diagnosis by said ultrasound.

44. The method as defined in claim 35 wherein pressure constitutes said external condition.

45. The method as defined in claim 44 further comprising the step of applying and/or removing said pressure for substantially less time than the time of physiological reaction of said living organism.

46. The method as defined in claim 45 further comprising the step of varying the time intervals between sequences of said applying and/or removing of said pressure.

* * * * *